United States Patent
Winkler et al.

(10) Patent No.: US 6,482,142 B1
(45) Date of Patent: Nov. 19, 2002

(54) ASYMMETRIC RADIATION DOSING APPARATUS AND METHOD

(75) Inventors: Rance A. Winkler, Atlanta; Timothy J. Patrick, Alpharetta, both of GA (US)

(73) Assignee: Proxima Therapeutics, Inc., Alpharetta, GA (US)

( * ) Notice: Subject to any disclaimer, the term of this patent is extended or adjusted under 35 U.S.C. 154(b) by 0 days.

(21) Appl. No.: 09/464,727

(22) Filed: Dec. 16, 1999

Related U.S. Application Data

(63) Continuation-in-part of application No. 09/293,524, filed on Apr. 15, 1999, which is a continuation-in-part of application No. 08/900,021, filed on Jul. 24, 1997, now Pat. No. 5,913,813.

(51) Int. Cl.$^7$ ................................................ A61N 5/00
(52) U.S. Cl. ......................................................... 600/3
(58) Field of Search ......................................... 600/1–8

(56) References Cited

U.S. PATENT DOCUMENTS

| | | | |
|---|---|---|---|
| 4,706,652 A | 11/1987 | Horowitz | 128/1.2 |
| 4,754,745 A | 7/1988 | Horowitz | 128/1.2 |
| 5,422,926 A | 6/1995 | Smith et al. | 378/121 |
| 5,562,594 A | 10/1996 | Weeks | 600/3 |
| 5,724,400 A | 3/1998 | Swerdloff et al. | 378/65 |
| 5,800,333 A | 9/1998 | Liprie | 600/3 |
| 5,803,895 A | 9/1998 | Kronholz et al. | 600/3 |
| 5,851,182 A | 12/1998 | Sahadevan | 600/407 |
| 5,863,284 A | 1/1999 | Klein | 600/3 |

FOREIGN PATENT DOCUMENTS

| | | | |
|---|---|---|---|
| WO | WO 97/19723 | 6/1997 | A61N/5/00 |

OTHER PUBLICATIONS

Ravinder, Nath, Ph.D. et al., Development of an $^{241}$Am Applicator For Intracavitary Irradiation of Gynecologic Cancers, I.J. Radiation Oncology, Biology, Physics, May 1988, vol. 14, No. 5, pp. 969–978.

Primary Examiner—John P. Lacyk
(74) Attorney, Agent, or Firm—Thomas J. Engellenner; Ronald E. Cahill; Nutter McClennen & Fish LLP

(57) ABSTRACT

An interstitial brachytherapy apparatus of the invention delivers radioactive emissions in an asymmetric fashion to target tissue surrounding a surgical extraction site. The apparatus includes an expandable outer surface element defining an apparatus spatial volume, a radiation source disposed within the apparatus volume, and a means for providing predetermined asymmetric isodose curves within the target tissue. In one configuration, asymmetric isodose curves are created in the target tissue by shaping or locating the radiation source so as to be asymmetrically placed with respect to a longitudinal axis of the apparatus. In other configurations, asymmetric radiopaque shielding is provided between the radiation source and the target tissue. A surgical procedure using the apparatus is also described.

14 Claims, 4 Drawing Sheets

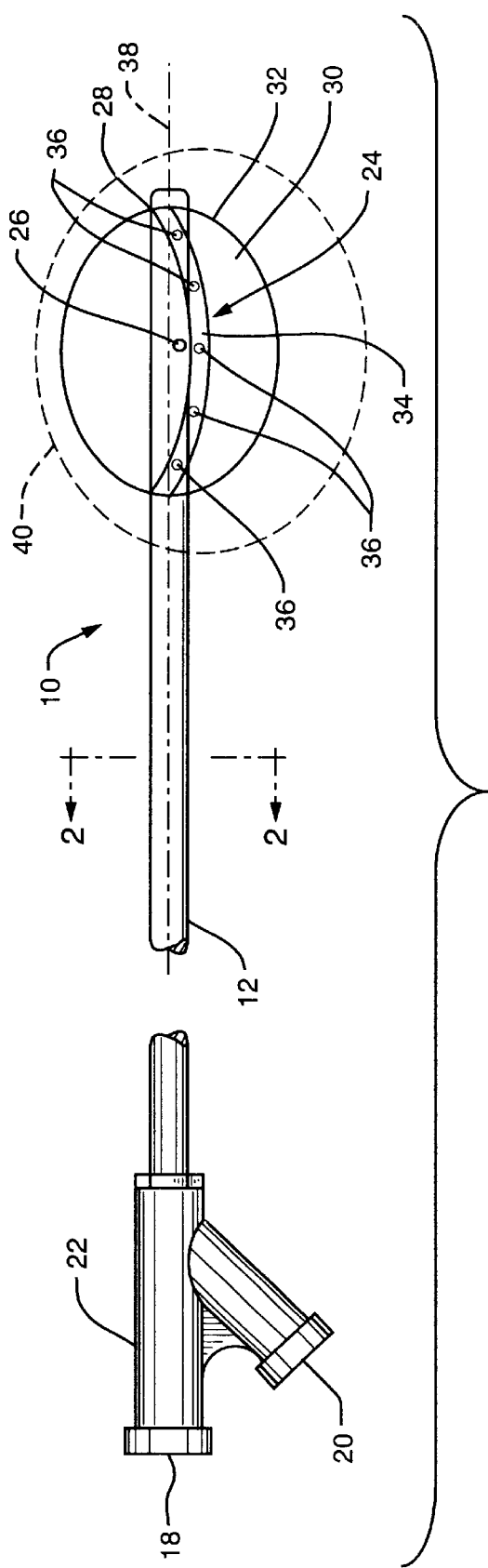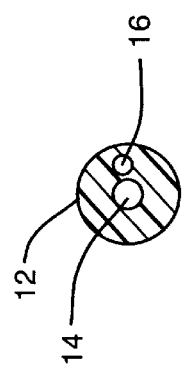
FIG. 1
FIG. 2

ASYMMETRIC RADIATION DOSING APPARATUS AND METHOD

CROSS-REFERENCE TO RELATED APPLICATIONS

This application is a continuation-in-part of co-pending U.S. patent application Ser. No. 09/293,524, filed Apr. 15, 1999, pending which is a continuation-in-part U.S. patent application Ser. No. 08/900,021, filed Jul. 24, 1997 (now issued as U.S. Pat. No. 5,913,813 to Williams et al.); the contents of these applications are specifically incorporated herein by reference.

BACKGROUND OF THE INVENTION

The, invention relates generally to an apparatus for use in treating proliferative tissue disorders, and more particularly to an apparatus for the treatment of such disorders in the body by the application of radiation.

Malignant tumors are often treated by surgical resection of the tumor to remove as much of the tumor as possible. Infiltration of the tumor cells into normal tissue surrounding the tumor, however, can limit the therapeutic value of surgical resection because the, infiltration can be difficult or impossible to treat surgically. Radiation therapy can be used to supplement surgical resection by targeting the residual tumor margin after resection, with the goal of reducing its size or stabilizing it. Radiation therapy can be administered through one of several methods, or a combination of methods, including external-beam radiation, stereotactic radiosurgery, and permanent or temporary interstitial brachytherapy. The term "brachytherapy," as used herein, refers to radiation therapy delivered by a spatially confined radioactive material inserted into the body at or near a tumor or other proliferative tissue disease site. Owing to the proximity of the radiation source, brachytherapy offers the advantage of delivering a more localized dose to the target tissue region.

For example, brachytherapy is performed by implanting radiation sources directly into the tissue to be treated. Brachytherapy is most appropriate where 1) malignant tumor regrowth occurs locally, within 2 or 3 cm of the original boundary of the primary tumor site; 2) radiation therapy is a proven treatment for controlling the growth of the malignant tumor; and 3) there is a radiation dose-response relationship for the malignant tumor, but the dose that can be given safely with conventional external beam radiotherapy is limited by the tolerance or normal tissue. In brachytherapy, radiation doses are highest in close proximity to the radiotherapeutic source, providing a high tumor dose while sparing surrounding normal tissue. Interstitial brachytherapy is useful for treating malignant brain and breast tumors, among others.

Interstitial brachytherapy is traditionally carried out using radioactive seeds such as $^{125}I$ seeds. These seeds, however, produce inhomogeneous dose distributions. In order to achieve a minimum prescribed dosage throughout a target region of tissue, high activity seeds must be used, resulting in very high doses being delivered in some regions in proximity to the seed or seeds which can cause radionecrosis in healthy tissue. One attempt to address this problem, at least with respect to limiting dosages to critical organs near the radioactive seed site, has been to provide a shield directly on a portion of the seed or on an applicator that holds the seed to shield the particularly sensitive tissue. (E.g., Nath et al., Development of an $^{241}Am$ Applicator for Intracavitary Irradiation of Gynecologic Cancers, *Intl. J. Radiation Oncology Biol. Phys.*, Vol., 14, pp. 969–978.) While this approach may be appropriate for some applications, it may still be overly "hot" for treating proximate tissue on the unshielded side of the seed, while not providing an effective dose on the shielded side of the seed.

Williams U.S. Pat. No. 5,429,582, entitled "Tumor Treatment," describes a method and apparatus for treating tissue surrounding a surgically excised tumor with radioactive emissions to kill any cancer cells that may be present in the tissue surrounding the excised tumor. In order to implement the radioactive emissions, Williams provides a catheter having an inflatable balloon at its distal end that defines a distensible reservoir. Following surgical removal of a tumor, the surgeon introduces the balloon catheter into the surgically created pocket left following removal of the tumor. The balloon is then inflated by injecting a fluid having one or more radionuclides into the distensible reservoir via a lumen in the catheter.

The apparatus described in Williams solves some of the problems found when using radioactive seeds for interstitial brachytherapy, but leaves some problems unresolved. The absorbed dose rate at a target point exterior to a radioactive source is inversely proportional to the square of the distance between the radiation source and the target point. s a result, where the radioactive source has sufficient activity to deliver a prescribed dose, say 2 centimeters into the target tissue, the tissue directly adjacent the wall of the distensible reservoir, where the distance to the radioactive source is very small, may still be overly "hot" to the point where healthy tissue necrosis may result. In general, the amount of radiation desired by the physician is a certain minimum amount that is delivered to a region up to about two centimeters away from the wall of the excised tumor. It is desirable to keep the radiation that is delivered to the tissue in the target treatment region within a narrow absorbed dose range to prevent over-exposure to tissue at or near the reservoir wall, while still delivering the minimum prescribed dose at the maximum prescribed distance from the reservoir wall. It is also desirable, at least in some applications, to provide these advantages while tailoring the radiation dosage to avoid fully dosing sensitive tissue or to reduce the amount of radiation that escapes the patient's body.

There its still a need for an instrument which can be used to deliver radiation from a radioactive source to target tissue within the human body with a desired intensity and at a predetermined distance from the radiation source without over-exposure of body tissues disposed between the radiation source and the target, and with the ability to shape the radiation dose to protect sensitive tissue or to protect against radiation exposure outside of the patient's body which may affect healthcare providers or others who might come close to the patient.

SUMMARY OF THE INVENTION

The present invention solves the problems described above by providing an interstitial brachytherapy apparatus for delivering radioactive emissions in an asymmnetric fashion to target tissue surrounding a surgical extraction site. The apparatus includes an expandable outer surface element defining an apparatus spatial volume, a radiation source disposed within the apparatus volume, and a means for providing predetermined asymmnetric isodose profile within the target tissue.

In one configuration, asymmetric isodose curves are created in the target tissue by shaping or locating the radiation source so as to be asymmetrically placed with respect to a longitudinal axis of the apparatus. In one example of an apparatus having this configuration, an inner volume containing a liquid radioisotope is asymmetrically placed within the apparatus volume so as to result in an isodose profile in the target tissue that is asymmetric about the longitudinal axis of the apparatus.

In another example, the radiation source comprises a plurality of spaced apart solid radioactive particles disposed within the apparatus volume and arranged to provide a predetermined asymmetric isodose curve within the target tissue. In one particular example, the plurality of spaced apart radioactive particles are provided on a single elongate member that is shaped so that some of the radioactive particles are farther from the longitudinal axis of the apparatus than others. In other particular examples, a plurality of members carrying radioactive particles are provided with at least one of the members being shaped so as to place at least one radioactive particle asymmetrically with respect to the longitudinal axis of the apparatus.

An interstitial brachytherapy apparatus of the invention may also be implemented in a device having an expandable outer surface defining an apparatus volume, a radiation source disposed within and spaced apart from the expandable outer surface, and at least one asymmnetric radiation shield spaced apart from the radiation source, the asymmetric radiation shielding resulting in predetermined asymmetric isodose curves with in the target tissue. In one embodiment, radiopaque shielding is provided on a portion of the expandable outer surface. In another embodiment, the radiation source is encompassed within a second, inner surface within the apparatus volume, with radiopaque shielding provided on at least a portion of the inner surface. In still further embodiments, one or more radiation shields are spaced apart from the radiation source and within the apparatus volume to achieve the desired asymmetric isodose distribution within the target tissue.

The invention also provides a method for treating a proliferating tissue disease using interstitial brachytherapy at an internal body location. The method includes surgically creating access to the proliferating tissue within a patient and surgically resecting at least a portion of the proliferating tissue to create a resection cavity within body tissue. An interstitial brachytherapy apparatus for delivering radioactive emissions as described above is then provided and intra-operatively placed into the resection cavity. After a prescribed absorbed dose has been delivered to tissue surrounding the apparatus, the apparatus is removed. The radioactive source material may be placed into the interstitial brachytherapy apparatus after the apparatus is placed in the resection cavity, and may be removed before the apparatus is removed. The method has particular applications to brain and breast cancers.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which:

FIG. 1 is a side view of an interstitial brachytherapy apparatus of the invention for delivering asymmetric radioactive doses to body tissue;

FIG. 2 is a cross-sectional view taken along the line 2—2 in FIG. 1;

DESCRIPTION OF THE PREFERRED EMBODIMENT

Figure 3:
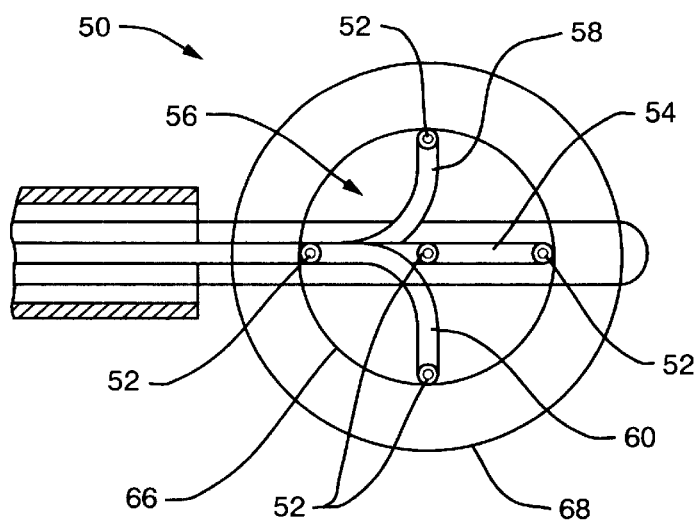
FIG. 3 is a side view of an additional embodiment of an interstitial brachytherapy apparatus of the invention.

A surgical instrument 10 for providing radiation treatment to proliferative tissue in a living patient is illustrated in FIG. 1. Surgical instrument 10 includes a tubular body member 12 having first and second lumens 14 and 16 (FIG. 2) extending from proximal ports 18 and 20 in a molded hub 22. The first lumen 14 carries a radioactive source 24 and second lumen 16 communicates with inflation port 26 formed through the side wall of the tube 12.

Affixed to the tubular body 12 proximate the distal end 28 thereof is an outer spatial volume 30 defined by an outer polymeric film barrier 32 that is appropriately spaced from the radioactive source 24. Outer volume 30 encompasses inflation port 26. With no limitation intended, the distensible polymeric film walls may comprise a biocompatible, radiation resistant polymer, such as silastic rubbers, polyurethanes, polyethylene, polypropylene, polyester, or PVC. The outer spatial volume 30 may be filled with air, saline or, alternatively, a radiation absorbing fluid, such as a contrast media used in angiography. Alternatively, the surface of outer volume 30 need not be a solid material. For example the surface of the outer volume 30 could be an expandable cage formed from a shape memory metal, such as nitinol, or a suitable plastic, such as an expandable polyethylene cage. Such a cage can be formed in the desired shape to conform to a particular isodose profile, contracted for delivery to the target site in vivo, then expanded to cause the tissue surrounding the surgically resected region to take the appropriate shape. The size of the outer spatial volume 30 generally will correspond approximately to the amount of tissue resected. For some applications, the size of the outer spatial volume 30 may be slightly smaller than the resected volume while for other applications, the outer spatial volume will be slightly larger than the resected volume, allowing the expandable surface of the outer spatial volume to urge tissue on the surface of the resected region into the appropriate shape to promote an even dose distribution around the outer spatial volume in the target tissue. In typical applications, the outer spatial volume has a diameter of approximately 2 to 6 centimeters.

Radiation source 24 comprises a wire 34 having one or more solid radioactive particles 36 located on the wire 34. For example, radioactive micro spheres of the type available from the 3M Company of St. Paul, Minn., may be used as the solid radioactive particles. Such a solid radioactive particle configuration offers an advantage in that it allows a wider range of radionuclides than if one is limited to liquids. Solid radionuclides that could be used with the delivery device of the present invention are currently generally available as brachytherapy radiation sources. Examples of radioactive materials which can be selected by a person of ordinary skills in the art for use with the present invention may be found in Tables 1 to 4 of PCT Publication WO 97/19723, which is hereby incorporated by reference.

The, radioactive source 24 can either be preloaded into the catheter at the time of manufacture, or loaded into the device after it has been implanted into the space formerly occupied by the excised tumor. If loaded after implantation, the solid radiation emitting material 36 can be inserted through lumen 14 on a wire 34, for example using an afterloader (not shown).

Radiation source 24 has an asymmetric configuration with respect to a longitudinal axis 38 of the instrument 10. That is, radiation source 24 is shaped so as to result in an isodose profile 40 that varies radially about the longitudinal axis 38. More simply, the isodose profile 40 of FIG. 1 has a shorter radius from the longitudinal axis 38 on the top side of the instrument 10 as shown in FIG. 1 than on the bottom side. The asymmetrically shaped isodose curve 40 may be created by providing a plurality of solid radioactive particles 36 on a curved wire 34 in a spaced apart relationship. This configuration will result in certain of the solid radioactive particles 36 being farther from the longitudinal axis 38 of the instrument 10 than others, and will result in the illustrated asymmetric isodose profile 40. One way to provide the illustrated radioactive source 24 configuration is to form wire 34 from a solid or tubular shape memory alloy such as nickel-titanium alloys known in the art to have such properties. Wire 34 can then be preformed to the desired shape, can be compressed into a substantially straight configuration to pass through lumen 14, and will resume its desired shape once inside volume 30 where wire 34 will be free from steric constraints imposed inside the lumen 14. The resulting asymmetric isodose curve 40 can be further tailored by using solid radioactive particles 36 having differing specific activities to achieve the desired dosing.

In,one embodiment, volume 30 and barrier 32 act to separate target tissue from the radiation source 24. Ideally, radiation therapy should make use the inherent difference in radiosensitivity between the tumor and the adjacent normal tissues to destroy cancerous tissue while causing minimal disruption to surrounding normal tissues. At high doses of radiation, however, the percentage of exposed cells that survive treatment decreases with first-order kinetics in proportion to increasing radiation dose. With increasing cell death comes increasing risk of necrosis or tissue death in healthy tissue that is treated with a high dose of radiation. Accordingly, it is desirable to keep the maximum radiation dose delivered by the brachytherapy apparatus as low as possible while still delivering the desired therapeutic dose to the desired range of tissue. One method for achieving this result is to provide a "hotter" radiation source in a spaced apart relationship to the target tissue. In this way, because the intensity of the radiation emitted by a source drops with the square of the distance from the source, the effective dosage may be maintained below necrosis levels in target tissue closest to the interstitial brachytherapy apparatus while providing the required dosage to a greater depth into the target tissue. (See, e.g., U.S. Pat. No. 5,913,813 which is hereby incorporated by reference in its entirety.) The capability of the apparatus of the invention to deliver absorbed doses deeper into the target tissue than prior interstitial brachytherapy devices while controlling the dose in proximity to the apparatus to reduce or eliminate the risk of healthy tissue necrosis allows for the use of brachytherapy in a greater number of cases.

For example, it is desirable to provide an interstitial brachytherapy device configured to provide a dose in a therapeutic range, say between 40 to 60 Gray, at a distance between 0.5 and 1.0 cm from the outer spatial volume for an outer spatial volume having a diameter of 4.0 cm and being in contact with the resection cavity wall. In a typical embodiment, the radioactive source material ranges from approximately 150 to 450 mCi in activity and encompasses most of the target treatment area with a 0.4 to 0.6 Gray/hour isodose contour. At this treatment rate, treatment may be completed in approximately 3 to 7 days, or more commonly, in approximately 3 to 5 days.

In some applications, the desired dosing profile is consistent with the shape of the outer volume 30. That is, the absorbed dose within the target tissue at points equidistant from the surface 32 of the outer spatial volume 30 should be substantially uniform in substantially every direction. Put another way, the three dimensional isodose profiles generated by the radiation source should be substantially similar in shape to the outer spatial volume 30. Where the apparatus of the invention is deployed in soft tissue, it may also be important for the surface 32 of the outer spatial volume 30 to be sufficiently firm so as to force the target tissue to take on the shape of the surface 30 so that the desired relationship between the isodose profiles and the target tissue is achieved While the interstitial brachytherapy device 10 of FIG. 1 may employ these techniques to positive effect, this device specifically alters the isodose profile for applications where particularly sensitive tissue or other concerns result in a desire to limit the dosage on one or more sides of the device as illustrated by isodose curve 40.

Figure 3A:
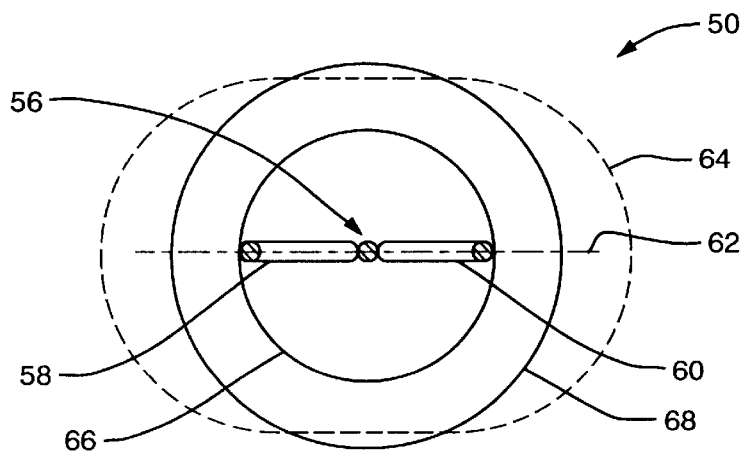
FIG. 3A is an end view of the interstitial brachytherapy apparatus of FIG. 3.

In a further embodiment of the brachytherapy device 50 of the invention, illustrated in FIG. 3, three solid radiation particles 52 are provided in a linear portion 54 of radiation source 56, while two additional radiation particles 52 are provided on co-planar extending portions 58, 60 of radiation source 56. An end view of the device 50 of FIG. 3 is shown in FIG. 3A with extending portions 58, 60 provided in a single plane 62, and resulting in isodose profile 64. A second inner, expandable surface 66 can also be provided within outer surface 68; the inner surface 66 enclosing the entirety of radiation source 56.

By providing extending portions 58, 60 having radioactive particles in the indicated co-planar relationship, areas of reduced dosage can be created on opposed sides of the device while maintaining symmetric dosing in all other directions. Of course, the number of sources and their configuration can be changed to create a desired asymmetric dosage. For example, an additional source could be added, for example above plane 62, to result in a symmetric isodose profile in all directions except the direction below the plane 62 which would have a lower dosage.

Figure 4:
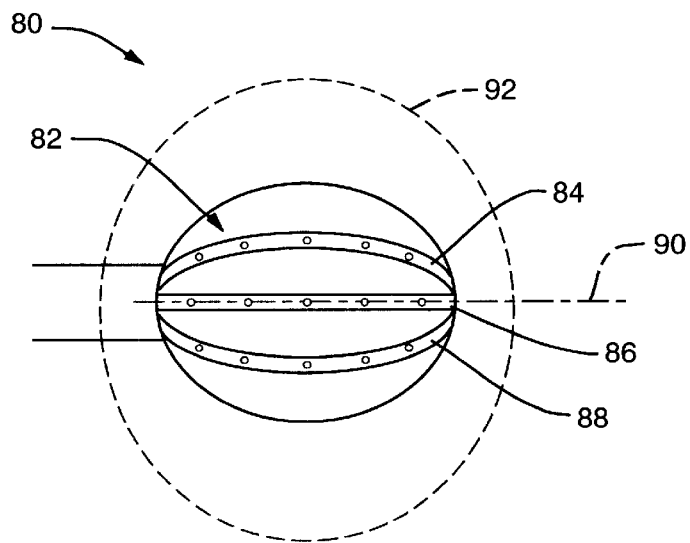
FIG. 4 is a side view of an additional embodiment of an interstitial brachytherapy apparatus of the invention.

An additional device 80 of the invention, shown in FIG. 4, includes a radiation source 82 that is made up of three wires 84, 86, 88, each having a plurality of solid radiation particles. Wire 86 is a straight wire extending along the longitudinal axis 90 of the device, while wires 84, 88 each curve as wire 34 described above with respect to FIG. 1. Wires 84, 88 are coplanar, resulting in an isodose profile 92 that is similar to isodose profile 64 of FIG. 3A. That is, the isodose profile will be symmetric in the plane in which the wires 84, 88 are disposed, but will have areas of reduced dosage in directions transverse to that plane (i.e., in FIG. 4, in the directions into and out of the page). As with the device 50 of FIGS. 3 and 3A, device 80 can be configured with more or fewer wires 84, 86, 88, and can be provided in configurations other than the depicted co-planar configuration in order to achieve desired asymmetric isodose profiles.

Figure 5:
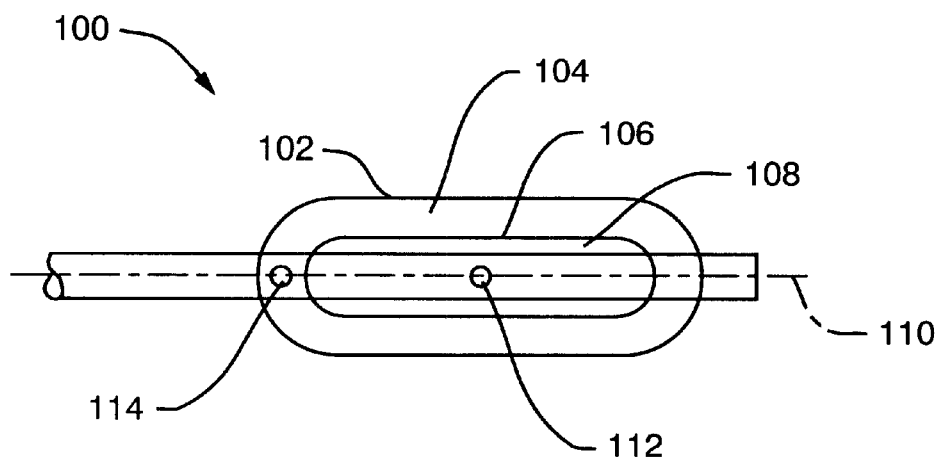
FIG. 5 is a side view of an interstitial brachytherapy apparatus of the invention configured for use with a liquid radiation source.

The asymmetric dosing effect achieved by the devices described above can also be achieved using a liquid radiation source. For example, device 100, illustrated in FIG. 5, has an outer surface 102 defining an outer volume 104 and an inner surface 106 defining an inner volume 108. The inner surface 106 is asymmetrically shaped or located with respect to the longitudinal axis 110 of the device 100 so as to result in the desired asymmetric dosing when the inner volume 108 is filled with a radioactive fluid. The inner volume 108 is spaced apart from the outer surface 102 and can be filled with a material containing a predetermined radionuclide, for example, I-125, I-131, Yb-169 or other source of radiation, such as radionuclides that emit photons, beta particles, gamma radiation, or other therapeutic rays. The radioactive material contained within the inner volume 108 can be a fluid made from any solution of radionuclide(s), e.g., a solution of Ir-192, I-125 or I-131. A radioactive fluid can also be produced using a slurry of a suitable fluid containing small particles of solid radionuclides, such as Au-198, Y-90. Moreover, the radionuclide(s) can be embodied in a gel. One radioactive material useful in the invention is lotrex™, a sterile single use, non-pyrogenic solution containing sodium 3-($^{125}$I)iodo-4-hydroxybenzenesulfonate ($^{125}$I-HIBS), available from Proxima Therapeutics, Inc. of Alpharetta, Ga. The inner volume 108 may be filled with radioactive fluid through port 112. Similarly, outer volume 104 can be filled on inflated using port 114.

A desired asymmetric dosing profile having the dosing characteristics described above may also be created by using asymmetric shielding between the radiation source and the target tissue as illustrated in FIGS. 6 through 9. In the device 120 of FIG. 6, a balloon 122 is located on the distal end of catheter 124. Radioactive particles 126 are disposed along the longitudinal axis 128 of the device. A portion of the surface, either inner or outer, of balloon 122 is coated with a radiopaque material 130 to result in asymmetric isodose curve 132. Radiopaque materials suitable for coating onto a polymeric surface of balloon 122 include, for example, barium, tungsten, bismuth, tantalum and tin.

Figure 6:
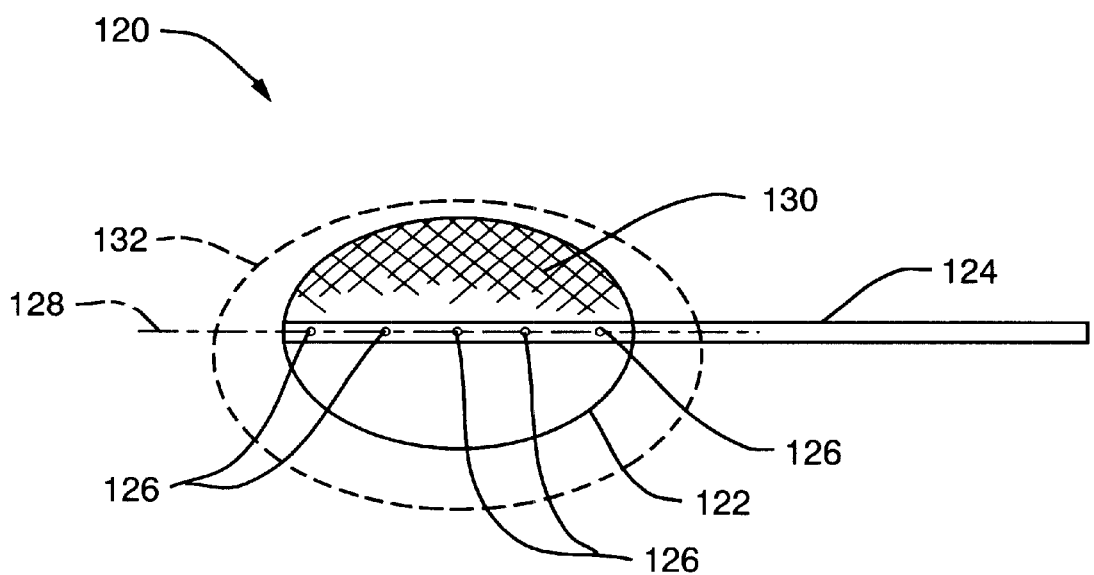
FIG. 6 is a side view of an interstitial brachytherapy device of the invention employing radiopaque coatings.
Figure 7:
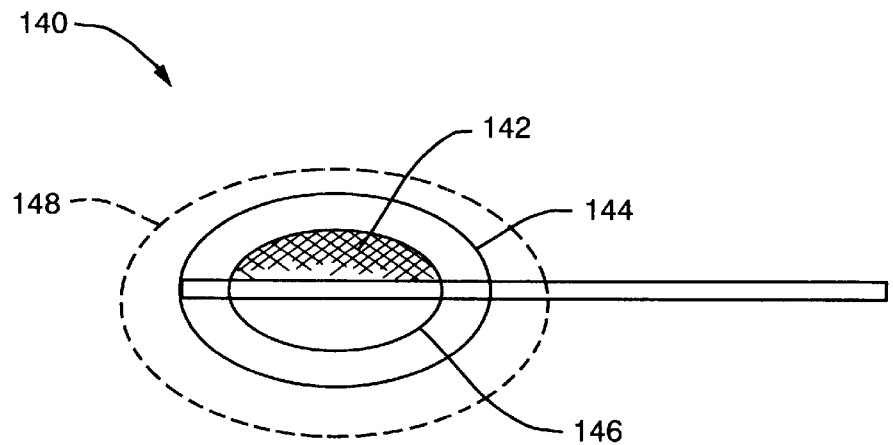
FIG. 7 is a side view of an interstitial brachytherapy device of the invention employing radiopaque coating and a liquid radiation source.

A further device 140 having radiopaque shielding 142 is illustrated in FIG. 7. Device 140 includes an outer volume surface 144 and an inner volume surface 146. Inner surface 146 may contain a liquid radiation source, or may enclose one or more solid particles as used in device 120 (FIG. 6). In device 140, the radiopaque material 142 is coated onto a portion of either the inner or outer side of the inner volume surface 146, resulting in a desired asymmetric isodose profile 148.

Figure 8:
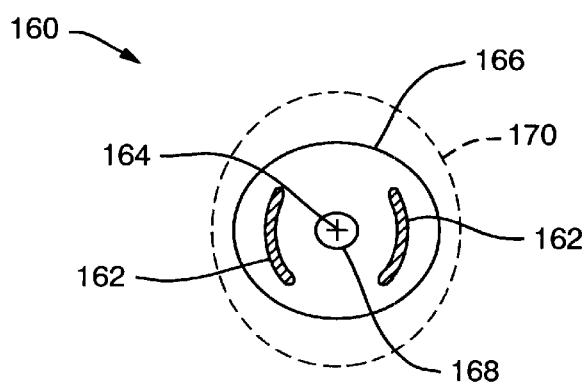
FIGS. 8 and 9 are end views of interstitial brachytherapy devices of the invention employing radiopaque shields.
Figure 9:
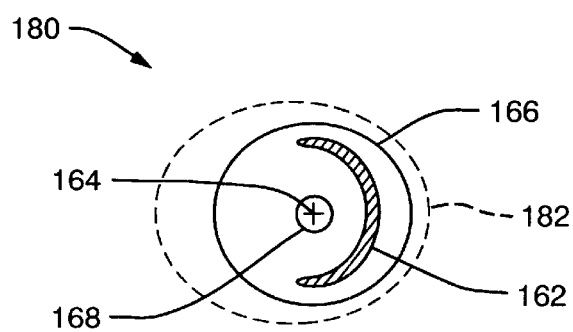

Additional devices 160, 180 of the invention having radiation shielding 162 are illustrated in FIGS. 8 and 9, respectively. In these devices 160, 180, one or more radiation shields 162 are provided between and spaced apart from a radiation source (not shown) located along a longitudinal axis 164 of the device and the target tissue, which will be located outside of expandable surface 166. The radiation source can include a liquid or a solid radiation source as described above. Shields 162 can be formed from radiopaque materials including those described above with respect to the radiopaque coating and can extend longitudinally from a base on the device located within the expandable surface 166.

As shown in FIG. 8, device 160 has two radiation shields 162 on opposed sides of catheter 168. This configuration results in lower radiation dosing on the two sides of the device 160 on which the shields 162 are located as shown by isodose curve 170. Device 180 (FIG. 9) has a single radiation shield 162 resulting in an asymmetric isodose curve 182 as shown. A person or ordinary skill in the art will recognize that other configurations may be employed to achieve desired isodose curves.

The interstitial brachytherapy apparatus of the invention can be used in the treatment of a variety of malignant tumors, and is especially useful for in the treatment of brain and breast tumors.

Many breast cancer patients are candidates for breast conservation surgery, also known as lumpectomy, a procedure that is generally performed on early stage, smaller tumors. Breast conservation surgery is typically followed by postoperative radiation therapy Studies report that 80% of breast cancer recurrences after conservation surgery occur near the original tumor site, strongly suggesting that a tumor bed "boost" of local radiation to administer a strong direct dose may be effective in killing any remaining cancer and preventing recurrence at the original site. The apparatus described herein can be used for either the primary or boost therapy. Numerous studies and clinical trials have established equivalence of survival for appropriate patients treated with conservation surgery plus radiation therapy compared to mastectomy.

Surgery and radiation therapy are also the standard treatments for malignant solid brain tumors. The goal of surgery is to remove as much of the tumor as possible without damaging vital brain tissue. The ability to remove the entire malignant tumor is limited by its tendency to infiltrate adjacent normal tissue. Partial removal reduces the amount of tumor to be treated by radiation therapy and, under some circumstances, helps to relieve symptoms by reducing pressure on the brain.

A method according to the invention for treating these and other malignancies begins by surgical resection of a tumor site to remove at least a portion of the cancerous tumor and create a resection cavity. Following tumor resection, but prior to closing the surgical site, the surgeon intraoperatively places an interstitial brachytherapy catheter apparatus, having an inner spatial volume and an outer spatial volume as described above but without having the radioactive source material loaded, into the tumor resection cavity. Once the patient has sufficiently recovered from the surgery, the interstitial brachytherapy catheter is loaded with a radiation source. The radioactive source dwells in the catheter until the prescribed dose of radiotherapy is delivered, typically for approximately a week or less. The radiation source is then retrieved and the catheter is removed. The radiation treatment may end upon removal of the brachytherapy apparatus, or the brachytherapy may be supplemented by further doses of radiation supplied externally.

It will be understood that the foregoing is only illustrative of the principles of the invention, and that various modifications can be made by those skilled in the art without departing from the scope and spirit of the invention, including, but not limited to, combinations of elements from different embodiments found herein. All references cited herein are expressly incorporated by reference in their entirety.

What is claimed is:

1. An interstitial brachytherapy apparatus for treating target tissue surrounding a surgical extraction comprising:

an expandable outer surface defining a three-dimensional apparatus volume configured to fill an interstitial void created by the surgical extraction of diseased tissue and define an inner boundary of the target tissue being treated;

a radiation source disposed completely within the expandable outer surface and located so as to be spaced apart from the apparatus volume, the radiation source further being asymmetrically located and arranged within the expandable surface to provide predetermined asymmetric isodose curves with respect to the apparatus volume.

2. A surgical apparatus for providing radiation treatment to target tissue comprising:

an expandable outer surface defining an apparatus volume;

a radiation source replaceably disposable within the expandable outer surface, the radiation source comprising a plurality of solid radiation sources arranged to provide predetermined asymmetric isodose curves within the target tissue, the plurality of solid radiation sources being provided in a spaced apart relationship on a single elongate member, the single elongate member being shaped to provide asymmetric placement of the spaced apart solid radiation sources with respect to a longitudinal axis through the apparatus volume.

3. The apparatus of claim 2, further comprising a catheter in communication with the apparatus volume, the elongate member extending through the catheter into the apparatus volume.

4. The apparatus of claim 3, wherein the elongate member is formed of a shape memory alloy, the elongate member being shaped to provide asymmetric placement of the spaced apart solid radiation sources, taking on a substantially straight shape while being inserted through the catheter to the apparatus volume, and resuming an asymmetric shape when extended into the apparatus volume.

5. A surgical apparatus for providing radiation treatment to target tissue comprising:

an expandable outer surface defining an apparatus volume;

a radiation source replaceably disposable within the expandable outer surface, the radiation source comprising a plurality of solid radiation sources arranged to provide predetermined asymmetric isodose curves within the target tissue, wherein at least one of the plurality of solid radiation sources has a different specific activity from at least one other solid radiation source.

6. A surgical apparatus for providing radiation treatment to target tissue comprising:

an expandable outer surface defining an apparatus volume;

a radiation source replaceably disposable within the expandable outer surface, the radiation source comprising a plurality of solid radiation sources arranged to provide predetermined asymmetric isodose curves within the target tissue, the plurality of radiation sources being provided on at least two elongate members extending into the apparatus volume, at least one of the elongate members being shaped to provide asymmetric placement of a radiation source with respect to a longitudinal axis through the apparatus volume.

7. The apparatus of claim 6, wherein each of the at least two elongate members includes a plurality of solid radiation sources provided in a spaced apart relationship.

8. The apparatus of claim 1, wherein the expandable outer surface is sufficiently rigid to deform the target tissue into the shape of the expandable outer surface, causing the predetermined asymmetric isodose curves to penetrate into the target tissue to a prescribed depth.

9. An interstitial brachytherapy apparatus for treating target tissue surrounding a surgical extraction comprising:

an expandable outer surface having a base and defining a three-dimensional apparatus volume configured to fill an interstitial void created by the surgical extraction of diseased tissue and define an inner boundary of the target tissue being treated;

a radiation source disposed completely within and spaced apart from the expandable outer surface; and an asymmetric radiation shield spaced apart from the radiation source, the asymmetric radiation shield providing predetermined asymmetric isodose curves with respect to the apparatus volume.

10. The apparatus of claim 9, wherein the asymmetric radiation shield comprises a radio-opaque material disposed on only a portion of the expandable outer surface.

11. The apparatus of claim 10, wherein the expandable outer surface comprises an inflatable balloon.

12. The apparatus of claim 11, wherein the radiation shield comprises a barium material disposed a portion of the inflatable balloon.

13. The apparatus of claim 9, further comprising at least one radiation shield extending from the base of the expandable outer surface toward an opposite end of the expandable surface, the shield being in between and spaced apart from the radiation source and the expandable outer surface, the shield forming a radio-opaque barrier between a portion of the radiation source and the target tissue.

14. The apparatus of claim 13, wherein the radiation shield comprises two shields provided on opposite sides of the radiation source.

* * * * *